(12) United States Patent
Jessop (10) Patent No.: US 9,539,073 B2
(45) Date of Patent: Jan. 10, 2017

(54) LOW PASS FILTER ATTACHMENTS FOR USE WITH DENTAL CURING LIGHTS

(75) Inventor: Neil Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 14/003,784

(22) PCT Filed: Mar. 9, 2012

(86) PCT No.: PCT/US2012/028437
§ 371 (c)(1),
(2), (4) Date: Sep. 6, 2013

(87) PCT Pub. No.: WO2012/122455
PCT Pub. Date: Sep. 13, 2012

(65) Prior Publication Data
US 2013/0344456 A1    Dec. 26, 2013

Related U.S. Application Data

(60) Provisional application No. 61/451,489, filed on Mar. 10, 2011.

(51) Int. Cl.
*A61C 13/15* (2006.01)
*A61K 6/027* (2006.01)

(52) U.S. Cl.
CPC ............. *A61C 19/004* (2013.01); *A61K 6/027* (2013.01)

(58) Field of Classification Search
CPC .................. A61C 19/003–19/004; A61K 6/027
USPC ........................................................ 433/29
See application file for complete search history.

(56) References Cited

U.S. PATENT DOCUMENTS

| | | | |
|---|---|---|---|
| 4,385,344 A | 5/1983 | Gonser | |
| 5,616,141 A * | 4/1997 | Cipolla | 606/15 |
| 6,171,105 B1 * | 1/2001 | Sarmadi | 433/29 |
| 6,186,780 B1 * | 2/2001 | Hibst et al. | 433/29 |
| 6,325,623 B1 * | 12/2001 | Melnyk et al. | 433/29 |
| 6,485,300 B1 * | 11/2002 | Muller et al. | 433/29 |
| 6,702,576 B2 * | 3/2004 | Fischer et al. | 433/29 |
| 6,981,867 B2 | 1/2006 | Cao | |
| 7,106,523 B2 * | 9/2006 | McLean et al. | 359/708 |
| 2004/0076921 A1 | 4/2004 | Gofman et al. | |
| 2004/0101802 A1 * | 5/2004 | Scott | 433/29 |
| 2005/0123877 A1 * | 6/2005 | Duret | B29C 35/0805 433/29 |
| 2006/0024638 A1 | 2/2006 | Rosenblood et al. | |
| 2006/0084028 A1 | 4/2006 | Cheetham | |
| 2007/0121786 A1 | 5/2007 | Okawa et al. | |
| 2007/0280888 A1 * | 12/2007 | Fujikawa et al. | 424/9.71 |
| 2010/0190129 A1 | 7/2010 | Paz | |

* cited by examiner

*Primary Examiner* — Cris L Rodriguez
*Assistant Examiner* — Hao D Mai
(74) *Attorney, Agent, or Firm* — Workman Nydegger (57) ABSTRACT

A dental curing light system is configured to include a dental curing light (100) having a device body (102) with a proximal handle portion (106) and a distal head portion (104). One or more light sources (120) for generating light are disposed on or within the device body (102). Generated light is emitted from the distal head portion (104) and includes wavelengths greater than about 420 nm and wavelengths less than 420 nm. A separate head attachment member or device (160) is coupleable over the distal head (110) of the device body (102) so as to receive substantially all light emitted from the distal head portion (104) of the device body (102).

30 Claims, 7 Drawing Sheets

LOW PASS FILTER ATTACHMENTS FOR USE WITH DENTAL CURING LIGHTS

CROSS-REFERENCE TO RELATED APPLICATIONS

This Patent Application is a U.S. National Stage of International Application No. PCT/US2012/028437, filed on Mar. 9, 2012, which claims priority to U.S. Provisional Application No. 61/451,489 filed on Mar. 10, 2011, the disclosures of which are incorporated herein by reference in their entireties.

BACKGROUND OF THE INVENTION

1. The Field of the Invention

The present invention is in the field of dental curing light devices and systems.

2. The Relevant Technology

In the field of dentistry, dental cavities or preparations are often filled and/or sealed with photosensitive polymerizable compositions that are cured by exposure to radiant energy, such as visible or UV light. These compositions, commonly referred to as light-curable compositions, are placed within dental cavity preparations or onto dental surfaces where they are subsequently irradiated by light. The radiated light causes photosensitive components within the compositions to initiate polymerization of polymerizable components, thereby hardening the light-curable composition within the dental cavity preparation or other dental surface.

Light-curing devices are typically configured with an activating light source, such as a quartz-tungsten-halogen (QTH) bulb or light emitting diodes (LEDs). QTH bulbs generate a broad spectrum of light that can be used to cure a broad range of polymerizable compositions. QTH bulbs generate substantial waste heat and require bulky surrounding structure to draw waste heat away from the bulb and to dissipate the waste heat.

Use of LED light sources has been a significant improvement in dental curing devices. LEDs are smaller than QTH bulbs and generally radiate light at a narrow range surrounding a specific peak wavelength. They often require significantly less input power to generate a desired output of radiation. In addition, LED light sources provide a longer life (e.g., tens of thousands of hours or more) than QTH bulbs.

BRIEF SUMMARY OF THE PREFERRED EMBODIMENTS

The present invention is directed to dental curing light systems including a dental curing light device and a separate head attachment member coupleable over a distal head of the dental curing light in which the head attachment member includes a low pass filter configured to filter out wavelengths greater than about 420 nm (preferably greater than about 410 nm) so as to allow only those wavelengths which are less than about 420 nm (preferably less than about 410 nm) to be transmitted to the irradiated object or material.

The dental curing light includes a device body having a proximal handle portion and a distal head portion, and one or more light sources disposed on or within the device body for generating light. The generated light is emitted from the distal head end of the device body and includes a range of wavelengths. A first portion of the generated light has a wavelength greater than about 420 nm (preferably greater than about 410 nm) and a second portion of the generated light has a wavelength less than about 420 nm (preferably less than about 410 nm). The head attachment member including the low pass filter is coupleable over the distal head portion of the device body so as to receive substantially all of the generated light emitted from the distal head portion of the device body. The low pass filter allows those wavelengths that are less than about 420 nm (preferably less than about 410 nm) to pass through the filter, while those wavelengths that are greater than about 420 nm (preferably greater than about 410 nm) are not transmitted. For example, they may be absorbed or reflected.

The head attachment member can independently be provided as a head attachment device to a user separate from a curing light device and may comprise features that permit the head attachment member to be couplable to the curing light device, such as a distal head portion of the curing light device.

The system advantageously provides curing light wavelengths configured to cure a variety of light-curable dental compositions. For example, many light-curable dental compositions include camphorquinone and are cured by exposure to wavelengths in the range of about 460 nm to about 470 nm. Other light-curable compositions (e.g., including proprietary photo-initiators) are cured by exposure to wavelengths in the range of about 400 nm to about 410 nm. As such, the dental curing light may include multiple LED dies configured to emit at different wavelengths so as to be capable of curing both types of light-curable compositions.

Restorative materials (e.g., composite filling materials, sealants, etc.) used in dental restorations are often colored so as to be substantially indiscernable relative to the adjacent natural tooth tissue. For example, they may be substantially tooth-colored. In other words, there may be little or no visual contrast exhibited between natural dental tissue and adjacent restorative materials. This is advantageous from the perspective of aesthetic acceptability to the patient, but it can make it difficult for the practitioner to readily ascertain which portions of a restored tooth are natural tissue and which portions are restorative material. The inventor has found that many restorative materials used in dental restorations exhibit higher, enhanced contrast (e.g., as a result of fluorescence) when exposed to light having a wavelength of less than about 410 nm (e.g., about 405 nm). Because adjacent natural tooth and soft tissues do not exhibit this phenomenon, the locations of restorative material can more easily be determined if it is illuminated with light having a wavelength less than about 410 nm (e.g., 405 nm). The enhanced contrast between natural tissues and restoration materials is particularly enhanced if the higher wavelengths (i.e., those greater than about 410 nm) are filtered out, leaving only the shorter wavelengths to illuminate the natural tissue and restorative materials. For example, glare is significantly reduced when low pass filtering is employed, and the contrast effect is even greater than without such filtering.

The system allows the practitioner to use the dental curing light for curing any of various light-curable dental compositions. By thereafter coupling the head attachment member over the distal head portion of the device body, the practitioner can then use the dental curing light as a diagnostic device, readily identifying those areas within a tooth that have been replaced or covered with a restorative material. The dental curing light system may be used with the low pass filter head attachment member in place to initiate light-curing of some light-curable dental compositions (i.e., those including photo-initiators that are triggered by exposure to shorter wavelength light having a wavelength less than about 410 nm).

However, use of a low pass filter may render the curing light ineffective for curing light-curable compositions that rely on camphorquinone to initiate curing. In such cases, the low pass filter head attachment member is removed during curing and replaced to convert the curing light into a diagnostic device. The low pass filter head attachment member is easily coupleable and removable from the distal head portion of the device body as desired so as to allow the practitioner to easily transition from one configuration to the other.

These and other benefits, advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Definitions

The term "light source" includes any structure that may be used to generate and emit light. Exemplary structures include, but are not limited to, LED(s). Broad spectrum light sources (e.g., a QTH bulb) or multiple narrow spectrum light sources (e.g., LEDs) configured to emit different wavelengths may also be employed to provide a broad spectrum light source.

The term "LED" includes any light emitting diode. It may include additional the electrical components in addition to the light emitting die as well as an integral lens or protective layer included in a typical LED structure. Accordingly, references made herein to embodiments of the dental curing light systems including head attachment members including a lens are made with reference to secondary lenses or lenses that are not otherwise integrally included as part of the LED structure.

The term "spectrum of light" refers to light that is monochromatic or substantially monochromatic, as well as light that falls within a range of wavelengths. The term "wavelength", when used in the context of the term "spectrum of light", refers to either the actual wavelength of monochromatic light or the dominant wavelength within a range of wavelengths.

As used in this specification and the appended claims, the singular forms "a," "an" and "the" include plural referents unless the context clearly dictates otherwise.

II. Introduction

The present disclosure encompasses dental curing light systems, which include a dental curing light device composed of a device body having a proximal handle portion and a distal head portion and one or more light sources disposed on or within the device body for generating curing light wavelengths. The one or more light sources are configured to generate a range of wavelengths, including a first portion of light having a wavelength less than about 420 nm (preferably less than about 410 nm) and a second portion of light having a wavelength greater than about 420 nm (preferably greater than about 410 nm).

The system further includes a head attachment member coupleable over the distal head portion of the dental curing light in which the attachment member includes a low pass filter configured to filter out wavelengths greater than about 420 nm (preferably greater than about 410 nm) so as to allow only those wavelengths less than about 420 nm (preferably less than about 410 nm) to be transmitted to an irradiated substrate or material. The head attachment member including the low pass filter is coupleable to the distal head portion of the device body so as to receive substantially all of the generated light emitted from the distal head portion of the device body.

The head attachment member can independently be provided as a head attachment device to a user separate from a curing light device and may comprise features that permit the head attachment member to be coupleable to the curing light device, such as a distal head portion of the curing light device.

Restorative materials such as composite filling materials and sealants are often formulated so as to have a color that does not readily contrast with that of natural tooth tissue. This is aesthetically desirable from the perspective of the patient but it can make it difficult to for the practitioner to easily ascertain which materials are natural dental material and which are restorative material. The inventor has found that many restorative materials exhibit higher, enhanced contrast (e.g., as a result of fluorescence) relative to natural dental tissues when exposed to light having a wavelength of less than about 410 nm (e.g., about 405 nm). Because adjacent natural tooth and soft tissues do not exhibit this phenomenon, the location(s) of restorative material can be easily determined if illuminated with light having a wavelength less than 410 nm (e.g., 405 nm). The enhanced contrast between natural dental tissues and restorative materials is particularly enhanced if the higher wavelengths (i.e., those greater than about 410 nm) are filtered out, leaving only the shorter wavelengths to illuminate the natural tissue and restorative materials. In addition, low pass filtering has been discovered to significantly reduce glare to the user, making the resulting fluorescent or other resulting contrast of the restorative materials even more apparent to the practitioner.

III. Exemplary Dental Curing Light Systems

A. Dental Curing Light Devices Having An LED Light Source

Any dental curing light device may be used in systems of the present invention. Preferred dental curing lights may include an LED light source. Examples of dental curing light devices that may be used in connection with the inventive systems are disclosed in U.S. Pat. No. 6,331,111 to Cao; U.S. Pat. No. 6,692,252 to Scott; U.S. Pat. No. 6,702,576 to Fischer et al.; U.S. Pat. No. 6,994,546 to Fischer et al.; U.S. Pat. No. 6,890,175 to Fischer et al.; U.S. application Ser. No. 10/301,158, filed Nov. 21, 2002, and entitled "Wide Bandwidth LED Curing Light"; and PCT application Ser. No. PCT/US09/069738 filed Dec. 29, 2009 and entitled "Dental Curing Light Having Unibody Design that Acts as a Heat Sink". For purposes of disclosing exemplary dental curing light devices, the foregoing patents and applications are incorporated by reference. One presently preferred dental curing light device is embodied by the VALO™ dental curing light of Ultradent Products, Inc., located in South Jordan, Utah.

The dental curing light device can be perfectly suitable for use (e.g., in curing a photocurable dental composition) without the head attachment member that includes the low pass filter. In this way, the separate, releasably coupleable head attachment member adds additional versatility to an otherwise simple dental curing light device.

Figure 1:
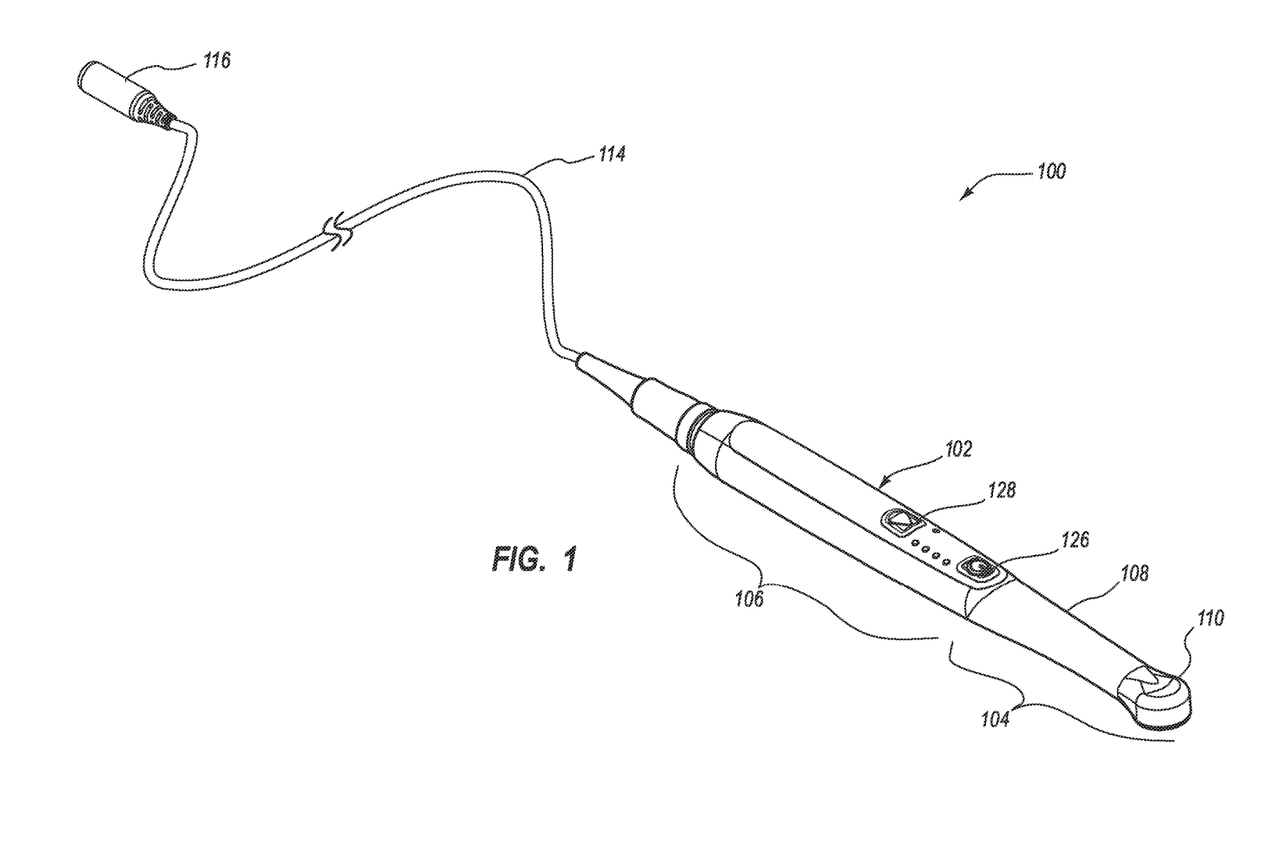
FIG. 1 is a top perspective view of an exemplary dental curing light device.
Figure 2:
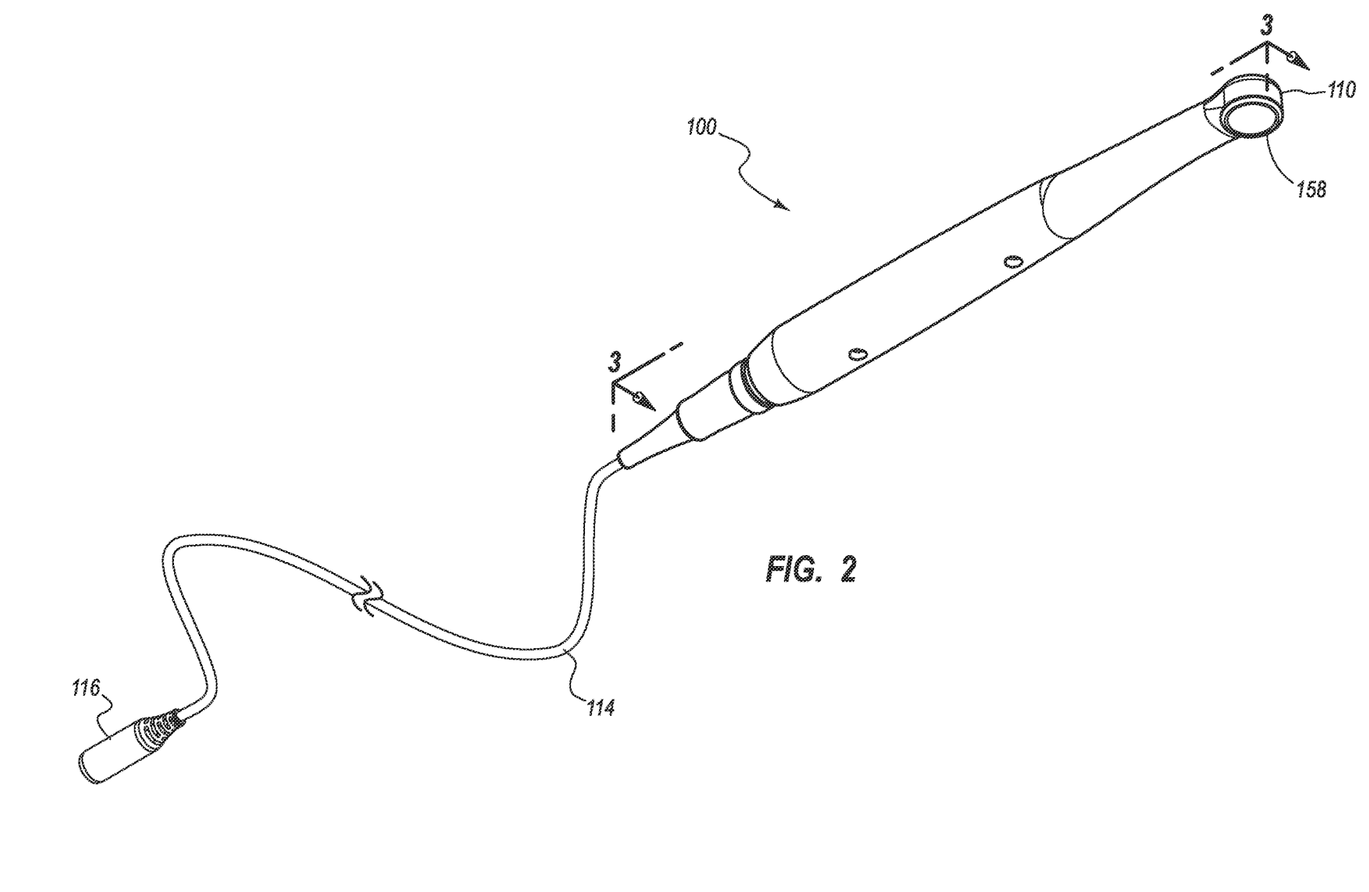
FIG. 2 is a bottom perspective view of the dental curing light device of FIG. 1.
Figure 3:
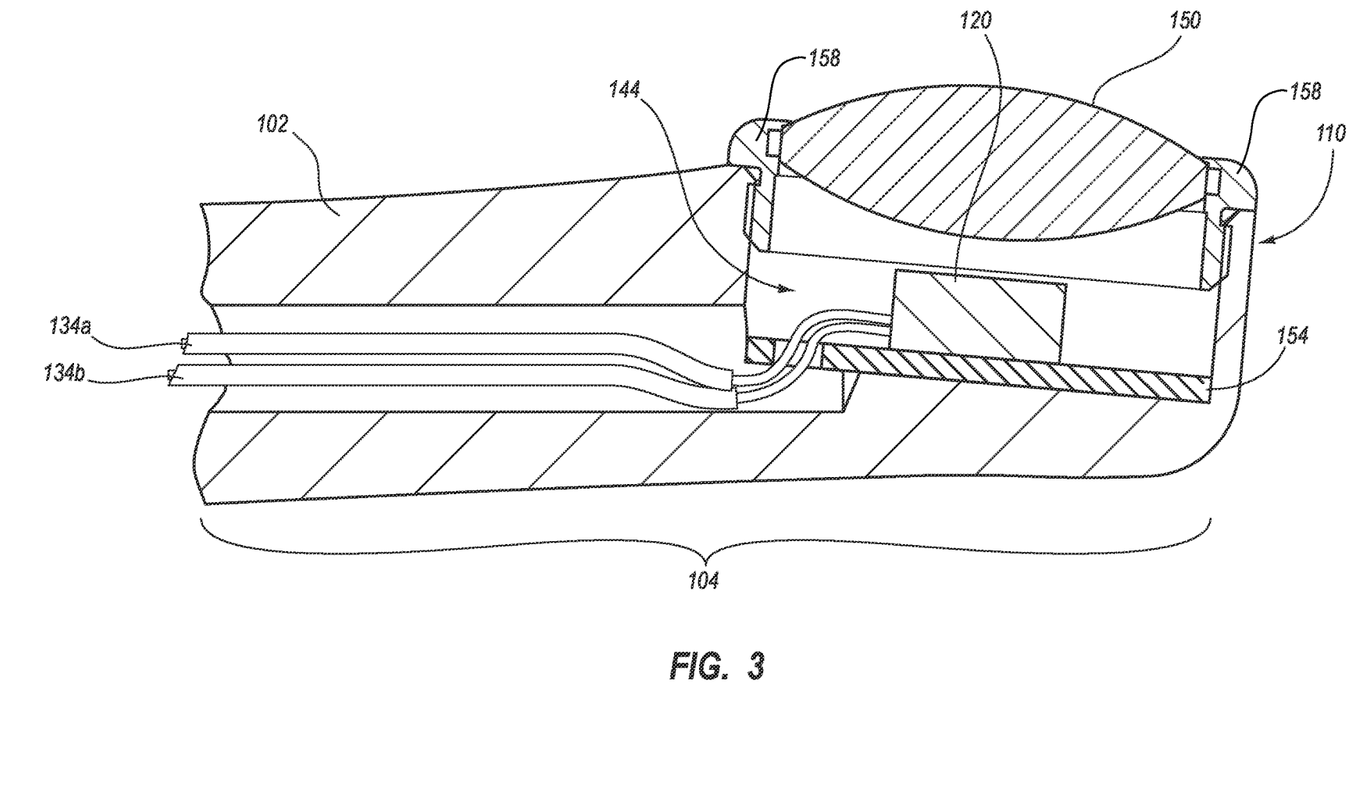
FIG. 3 is a cross-sectional view of the distal head portion of the dental curing light device of FIG. 1.

Reference is now made to FIGS. 1-3, which illustrate an exemplary dental curing light device 100 including an LED light source. As shown, the dental curing light device 100 may have the general configuration of an elongate dental hand piece with a sleek and slender device body 102 having a distal head portion 104 and a proximal handle portion 106. Distal head portion 104 may include a neck subportion 108 and a head subportion 110. Distal head portion 104 may be sized and configured to be inserted into the mouth of a dental patient.

Curing light 100 may include a power cord 114 having a plug 116 that allows the device to be coupled to a power source. In an alternative embodiment, the dental curing light can have a rechargeable battery or capacitor that powers an internal electronics assembly.

The dental curing light 100 may include an electronics assembly (not shown) connected to power cord 114 and that works in conjunction with power button 126 and intensity selector 128. Power button 126 allows the dental practitioner to power the curing light 100 on and off. Intensity selector 128 allows the dental practitioner to increase the intensity of the light being emitted from one or more LEDs or other light source(s) in head subportion 110. Actuating intensity selector 128 increases the power delivered to the light source(s). To decrease power intensity, the user can selectively power the curing light 100 off and back on again or this can be done automatically. Alternative control and operation modes will be readily apparent to one of skill in the art.

FIG. 2 shows a bottom perspective view of dental curing light 100, while FIG. 3 shows a cross-sectional view of the distal head portion 104. Head subportion 110 includes one or more light sources (e.g., LEDs) 120. LEDs 120 are configured to emit light at one or more wavelengths suitable for curing a light curable dental composition in the mouth of a patient. Wires 134a and 134b connect the electronics assembly (not shown) with the one or more LEDs or other light sources 120. The use of alternative power connections (e.g., electrically conductive traces) are also within the scope of the disclosure.

As described above, device body 102 includes a handle or gripping portion 106 that is sized and configured so as to permit a dental practitioner to hold and manipulate the device with the hand. Handle portion 106 may typically be rounded and substantially wider than neck subportion 108, which may advantageously be configured for insertion into a mouth of a patient. Neck subportion 108 is preferably narrow and elongate for minimizing the space necessary to manipulate the curing light 100 in the patient's mouth. Head subportion 110 may be somewhat wider than neck subportion 108, depending on the space required for the one or more LEDs (in embodiments where the LEDs are mounted on or within head 110). As shown in FIG. 3, head subportion 110 may include a recess or cavity 144 housing the LED(s) 120. Additional exemplary details regarding the illustrated dental curing light 100, as well as alternative dental curing light configurations, are disclosed in PCT application Ser. No. PCT/US09/069738 filed Dec. 29, 2009 and entitled "Dental Curing Light Having Unibody Design that Acts as a Heat Sink".

The LEDs themselves may comprise one or any number of suitable LEDs configured to emit wavelengths greater than about 420 nm (preferably about 410 nm) and wavelengths less than about 420 nm (preferably about 410 nm). For example, the light source may include two or more LEDs configured to emit at different wavelengths (e.g., one LED emits at greater than about 420 nm (preferably greater than about 410 nm) and one LED emits at less than about 420 nm (preferably less than about 410 nm)). In one embodiment, the dental curing light includes a first LED configured to emit light having a wavelength of about 405 nm, and a second LED configured to emit light having a wavelength of about 460 to about 470 nm. A third LED may be configured to emit light having an intermediate wavelength between about 445 nm and about 455 nm. Exemplary LED dies include inorganic solid-state LED dies and organic LED dies. Organic LED (OLED) dies are light emitting diodes whose emissive electroluminescent layer includes a film of organic compounds. The layer may typically include a polymer that allows suitable organic compounds to be deposited. The organic compounds are deposited in rows and columns onto a flat carrier.

FIG. 3 illustrates the components surrounding exemplary LED light source 120 at the distal head 110 in greater detail. Head subportion 110 may support or contains LED(s) or other light source(s) 120. Exemplary LED 120 is shown mounted on a thermally conductive layer 154. It is noted that the illustrated embodiment may include no heat sink other than body 102, which may be formed of a thermally conductive material such as aluminum. In embodiments where device body 102 comprises a material other than a thermally conductive material, an internal heat sink may be provided in thermal contact with light source(s) 120. In addition to any lens or protective cover included with light source 120, an additional lens 150 may be provided. A retaining ring 158 is shown surrounding lens 150 so that ring 158 fixedly retains lens 150 in place. Retaining ring 158 may be formed of a material that is magnetically attractable so that a magnet within the head attachment member can be magnetically retained over head subportion 110. Of course, other coupling mechanisms (e.g., a friction fit or any mechanical locking mechanism such as a snap fit, etc.) may be employed, as will be apparent to one of skill in the art in light of the present disclosure.

Figure 4:
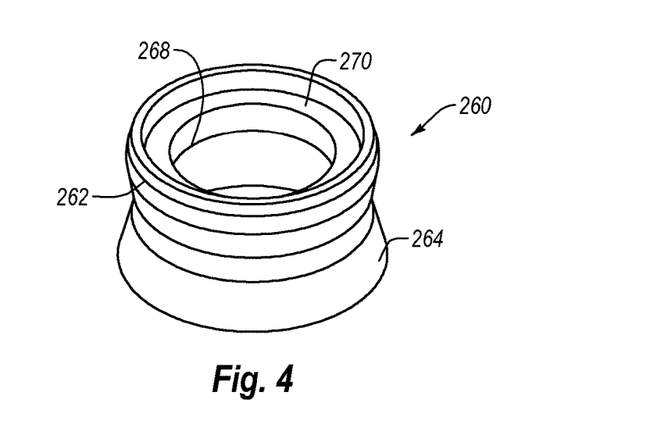
FIG. 4 is a perspective view of an exemplary head attachment member including a low pass filter for coupling over the distal head portion of the dental curing light device of FIG. 1.
Figure 5:
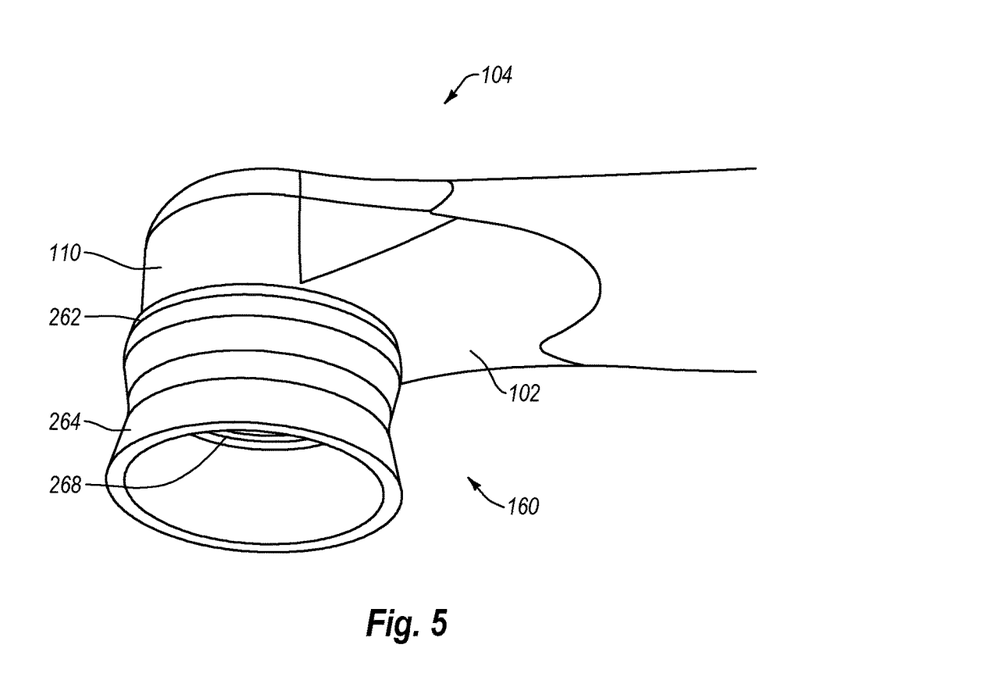
FIG. 5 is a perspective view of the exemplary head attachment member of FIG. 4 coupled over the distal head portion of the dental curing light device of FIG. 1.

It is noted that dental curing light device 100 is suitable for use (e.g., in curing any desired photocurable dental composition) by itself, without the attachment of the separate head attachment member (FIGS. 4-5). The head attachment member serves to filter out wavelengths greater than about 420 nm (preferably about 410 nm) from the generated light such that only those wavelengths having a wavelength less than about 420 nm (preferably about 410 nm) are transmitted through the head attachment member comprising a low pass filter. This characteristic has been found by the inventor to render the emitted light particularly suitable for the purpose of enhancing contrast between natural tooth tissue versus restorative materials. It may also provide other functionality, such as providing selective curing of curable materials designed to cure when irradiated with light having a wavelength less than 410 nm while not curing a curable material that only cures when irradiated with wavelengths that have been filtered out.

In summary, the dental curing light without the head attachment member coupled thereto provides a wider spectrum of emitted light, which may be suitable for curing, for example, both camphorquinone containing photocurable dental compositions (e.g., cured upon exposure to light having a wavelength between about 460 nm and about 470 nm) as well as proprietary photoinitiator containing photocurable dental compositions (e.g., cured upon exposure to light having a wavelength of about 405 nm). Upon coupling the head attachment member comprising the low pass filter over the distal head 110, the wavelengths greater than 410 nm are filtered out, meaning that the system is no longer suitable for use in curing camphorquinone containing photocurable dental compositions (or other materials that only cure if exposed to wavelengths that have been filtered out).

When the low pass filter is attached to the curing light, the curing system is now useful as a diagnostic tool in allowing the practitioner to easily discern between natural tooth tissues and restorative materials, even when adjacent to one another, and which appear seamless and substantially identical under ambient lighting conditions. For example, the inventor has found that by reducing the spectral width of emitted light to that portion that is less than about 420 nm (preferably less than about 410 nm), overall glare to the practitioner's eyes is reduced and contrast between such disparate materials is greatly enhanced. The head attachment member is advantageously removable so as to allow the practitioner to avail him or herself of the advantages of a widespectrum dental curing light (i.e., ability to cure a variety of photocurable dental compositions) while also providing the identification/diagnostic benefits associated with low pass filtering of the generated light when desired.

B. Exemplary Head Attachment Members/Devices

The dental curing light system includes a dental curing light device and a separate, removable head attachment member or device comprising a low pass filter configured to filter out wavelengths less than about 420 nm (preferably less than about 410 nm) from the generated light. FIG. 4 shows a head attachment member 260 configured as a light shield including a body 262 including a proximal end that is generally configured as a cylinder, and includes an outwardly flared skirt 264 disposed at the distal end of body 262. The exterior surfaces of body 262 and skirt 264 may be opaque so as to shield or prevent light from being transmitted through these surfaces. Although illustrated as having a particular shape and configuration, it will be understood that head attachment member 260 may be differently shaped and/or configured.

Any coupling mechanism may be employed for releasable coupling of head attachment member 260 over distal head 110. According to one embodiment, a magnetic mechanism may be used for releasably coupling head attachment member 260 over distal head 110. A magnet 270 may be disposed within body 262 near the proximal end of body 262, supported by rim 268. Magnet 270 may be friction fit, glued, or otherwise fixed relative to body 262. Light shield attachment member 260 may be magnetically coupled over the distal head 110 of dental curing light 100 as a result of magnetic attraction between magnet 270 and retaining rim 158 (or another portion of head 110). Magnet 270 is one example of a mechanism or means for coupling head attachment member 260, although other alternative attachment mechanisms or means will be apparent to one of skill in the art in light of the present disclosure. For example, a friction fit, or any type of mechanical locking mechanism (e.g., snap fit) may be employed.

FIG. 5 illustrates the distal head 110 with head attachment member 160 coupled over head 110 so that substantially all light generated by one or more LEDs 120 is received into head attachment member 160. In this manner, head attachment member 160, when coupled to a curing light, filters out those wavelengths greater than about 420 nm (preferably greater than about 410 nm), while allowing only those wavelengths less than about 420 nm (preferably less than about 410 nm) to be transmitted through the low pass filter of head attachment member 160. Head attachment member 160 may be formed of any desired material, examples of which include, but are not limited to, acrylic, polyacrylic, polypropylene, polycarbonate, silicone, aluminum dioxide, sapphire, quartz, and glass.

A low pass filter is included within head attachment member 160. For example, a material configured to filter out wavelengths greater than about 420 nm (preferably greater than about 410 nm) may be incorporated into the forming material. The low pass filter may comprise an absorptive material configured to absorb wavelengths greater than about 420 nm (preferably greater than about 410 nm), while allowing shorter wavelengths to pass through (i.e., be transmitted). In another embodiment, the low pass filter may comprise a material configured to reflect wavelengths greater than about 420 nm (preferably greater than about 410 nm), while allowing shorter wavelengths to be transmitted. In another embodiment, a combination of absorption and reflection may result in transmission of only the desired wavelengths (i.e., those less than about 410 nm). Exemplary low pass filtering materials (e.g., color filters) are available from Rosco Laboratories, Inc., located in Stamford, Conn. and Oasis Stage Werks, located in Salt Lake City, Utah. Such color filtering materials may comprise a reflective or absorbing dye or pigment molded with a plastic resin material (e.g., including, but not limited to polycarbonate and/or polyester) or glass.

Figure 7:
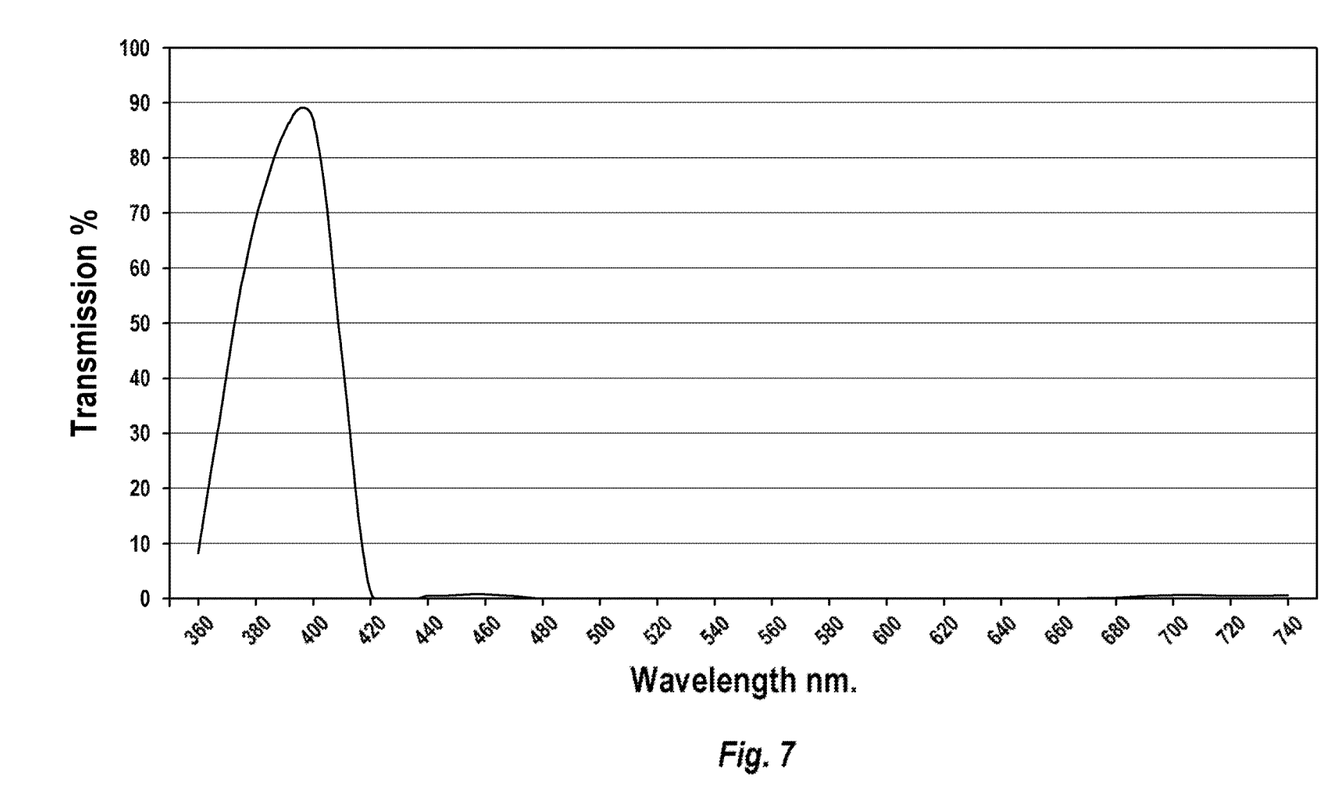
FIG. 7 is a graph illustrating the transmission characteristics of an exemplary low pass filter.

In another embodiment, the low pass filter may comprise a substrate including a dichroic coating configured to reflect (or absorb) unwanted wavelengths of light, allowing only wavelengths lower than the cut off wavelength to be transmitted. The transmission characteristics of one such exemplary low pass dichroic filter are presented in FIG. 7, in which the low pass filter only transmits wavelengths between about 360 nm and about 420 nm. More specifically, peak transmittance of almost 90% (e.g., about 87%) is at about 400 nm, and drops off quickly at higher wavelengths. For example, transmittance may be only about 1% at 420 nm and only about 30% at about 410 nm. Transmittance at higher wavelengths (e.g., from about 420 nm to about 740 nm) is substantially zero.

In one embodiment, the low pass filter may also filter out harmful short wavelength UV wavelengths. Such a configuration may be beneficial where it is desired to limit exposure to wavelengths shorter than about 350 nm. For example, the filter shown in FIG. 7 only has about 8% transmission of 360 nm wavelength light, and rising to about 70% transmission at 380 nm.

In one embodiment, such a dichroic filter may comprise a glass substrate (e.g., borosilicate glass such as BOROFLOAT or TEMPAX, available from Schott Corporation, located in Yonkers, N.Y. Exemplary glass substrates may have a thickness ranging between about 0.5 mm and about 5 mm, more preferably between about 0.75 mm and about 4 mm, and most preferably between about 1 mm and about 3 mm (e.g., about 1.75 mm). Alternating layers of different materials, for example, a relatively high refractive index layer and a lower refractive index layer may be deposited or otherwise applied to the substrate. Exemplary layers include silicon dioxide as a relatively low refractive index layer and titanium dioxide as a relatively high refractive index layer. Other coating layer materials, such as gold and molybdenum will be apparent to those of skill in the art in light of the present disclosure. Typically a plurality of alternating layers may be applied (e.g., at least about 4). Such layers may be approximately equal in thickness or alternatively may be of different thicknesses. Such layers may be applied by any suitable technique, including various deposition techniques, including chemical deposition (e.g., chemical vapor deposition), physical deposition, and combinations thereof. In one embodiment, only one side or both sides of the substrate may include the dichroic coating In one embodiment, the thickness of each dichroic layer may have an optical thickness varying between about 0.1 angstroms and about 1 angstrom. The total thickness applied to one side may be between about 0.5 microns and about 2 microns, more typically between about 0.75 micron and about 1.5 microns.

In one embodiment, transmission of the desired wavelengths is at least about 40%, preferably at least about 50%, more preferably at least about 60%, more preferably at least about 70%, more preferably at least about 80%, and most preferably at least about 85%. Similarly, transmission of the filtered out wavelengths (i.e., those greater than about 420 nm, preferably greater than about 410 nm) is no more than about 25%, preferably no more than about 10%, and most preferably no more than about 3%. In one embodiment, transmission of the filtered out wavelengths is substantially zero. In a preferred embodiment, the filtered out wavelengths are reflected rather than absorbed.

Figure 6A:
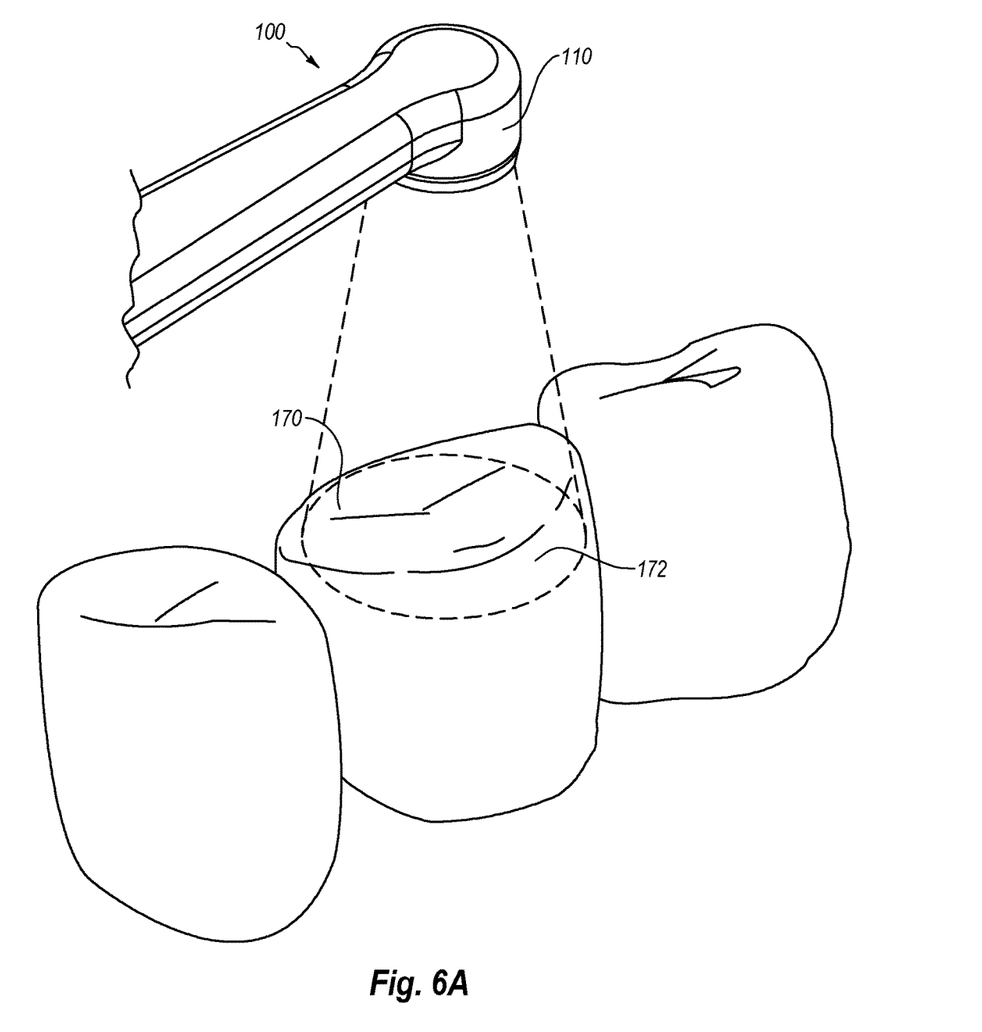
FIG. 6A is a perspective view of just the distal head portion (i.e., without the low pass filter head attachment member attached) of the dental curing light of FIG. 5 schematically showing the footprint of illumination onto a tooth and showing no substantial difference in contrast between restoration materials in the tooth and adjacent natural tooth tissue.
Figure 6B:
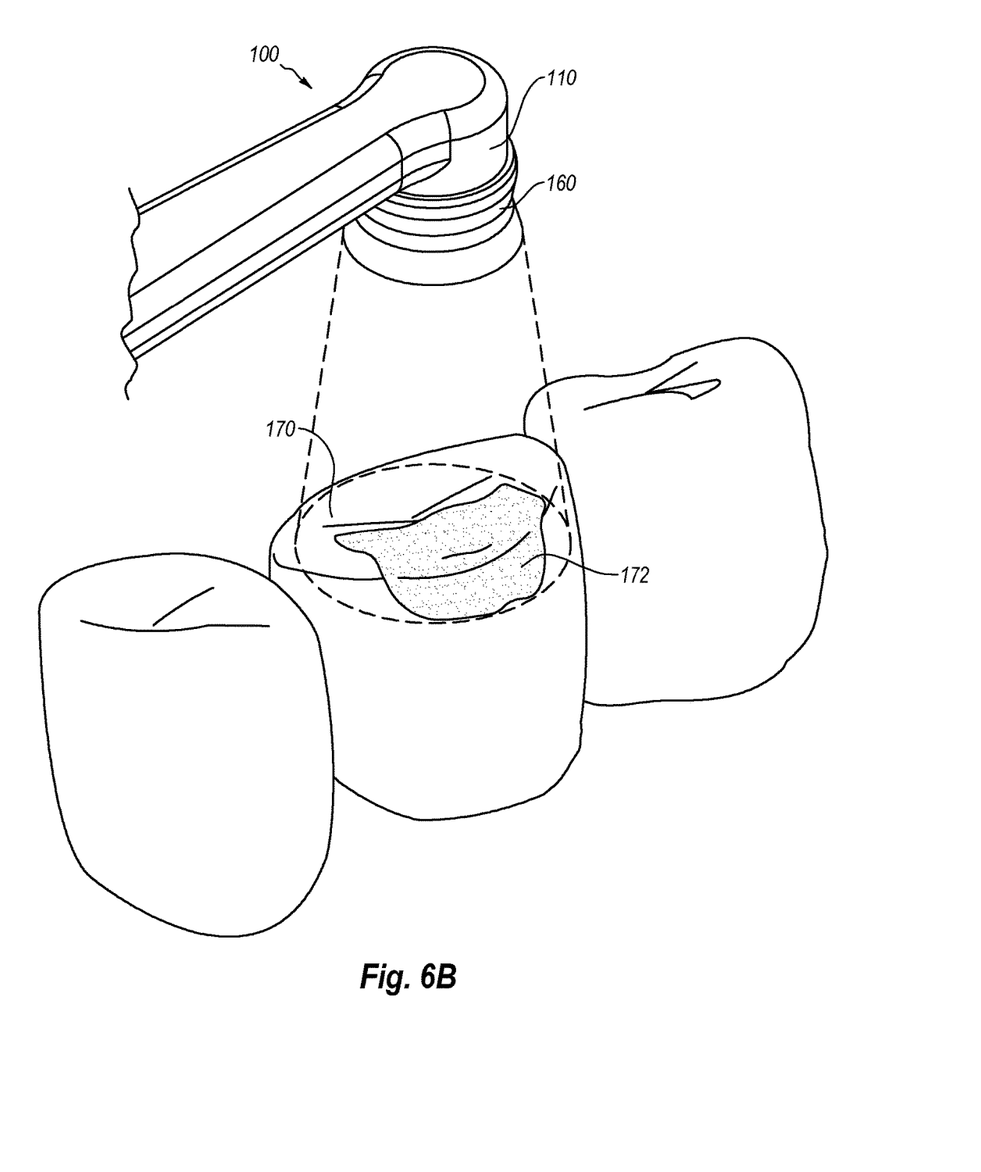
FIG. 6B is a perspective view of the distal head portion with the low pass filter head attachment member attached and showing the footprint of illumination onto the tooth of FIG. 6A showing the restoration material contrasted relative to the adjacent natural tooth tissue.

As seen in FIGS. 5 and 6B, head attachment member 160 preferably attaches so that the longitudinal axis of the attachment member 160 is non-parallel (e.g., substantially perpendicular) relative to the longitudinal axis of the body of the dental curing light device 100.

As shown in FIG. 6B, when dental curing light 100 is activated and head attachment member 160 is coupled, an emitted footprint of light is able to provide or enhance a contrast between natural tooth tissue 170 and restorative material 172. As seen in FIG. 6A, when ambient light, or even unfiltered light from dental curing light 100 is directed onto the same natural tooth tissue 170 and restorative material 172, there is little or no visual contrast between the different materials. Upon use of the low pass filter as illustrated in FIG. 6B, only those wavelengths less than about 420 nm (preferably about 410 nm) are allowed to be transmitted through head attachment member 160. This permits the practitioner to easily discern between natural tissue 170 and the restorative material 172. Although perhaps not completely understood, this phenomenon may be the result of components within the restorative material 172 that cause it to fluoresce as a result of exposure to the relatively narrow spectrum light. This contrast is easily visible even when some ambient light (e.g., as normally present within the practitioner's room) is present. This may be as a result of the significantly higher intensity of the narrow spectrum light emitted from low pass filtered dental curing light 100 within the patient's mouth compared to the ambient light.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A dental curing light system, comprising:
a dental curing light device comprising:
a device body having a proximal handle portion and a distal head portion from which light is emitted during use; and
one or more light sources disposed on or within the device body and that are configured for generating light that includes wavelengths of light greater than about 420 nm and wavelengths of light less than about 420 nm; and
a head attachment member coupleable to the distal head portion of the device body and configured so as to receive substantially all light emitted from the distal head portion of the device body,
the head attachment member comprising a low pass filter configured to filter out wavelengths of light greater than a specified wavelength and transmit substantially all wavelengths of light less than the specified wavelength, wherein the specified wavelength is about 420 nm or less such that and substantially no wavelengths of light greater than the specified wavelength of about 420 nm or less are transmitted through the low pass filter and substantially all wavelengths of light less than the specified wavelength of about 420 nm or less are transmitted through the low pass filter.

2. A dental curing light system as recited in claim 1, wherein the one or more light sources comprise one or more LEDs.

3. A dental curing light system as recited in claim 2, wherein the one or more light sources comprise a plurality of LEDs including a first LED configured to generate light having a wavelength less than about 420 nm and a second LED configured to generate light having a wavelength greater than about 420 nm.

4. A dental curing light system as recited in claim 3, wherein the first LED is configured to generate light having a wavelength of about 405 nm and the second LED is configured to generate light having a wavelength between about 460 nm and about 470 nm.

5. A dental curing light system as recited in claim 4, further comprising a third LED configured to generate light having a wavelength between about 445 nm and about 455 nm.

6. A dental curing light system as recited in claim 1, wherein the low pass filter of the head attachment member comprises a dichroic coated substrate configured to reflect wavelengths greater than about 420 nm.

7. A dental curing light system as recited in claim 1, wherein the low pass filter is configured to filter out wavelengths greater than about 410 nm.

8. A dental curing light system as recited in claim 1, wherein transmission of wavelengths that are not filtered out by the low pass filter is at least about 50%.

9. A dental curing light system as recited in claim 1, wherein transmission of wavelengths that are filtered out by the low pass filter is substantially zero.

10. A dental curing light system, comprising:
a dental curing light device comprising:
a device body having a proximal handle portion and a distal head portion from which light is emitted during use; and
first and second LEDs disposed on or within the device body that are configured for generating light, the first LED being configured to generate light having a wavelength less than about 410 nm and the second LED being configured to generate light having a wavelength greater than about 410 nm,
the generated light being emitted from the distal head portion of the device body; and
a head attachment member coupleable to the distal head portion of the device body and configured so as to receive substantially all light emitted from the distal head portion of the device body,
the head attachment member comprising a low pass filter configured to filter out wavelengths of light greater than about 410 nm from the generated light and transmit substantially all wavelengths of light less than about 410 nm such that substantially all wavelengths of light less than about 410 nm are transmitted through the low pass filter and substantially no wavelengths of light greater than about 410 nm are transmitted through the low pass filter.

11. A dental curing light system as recited in claim 10, wherein the first LED is configured to generate light having a wavelength of about 405 nm and the second LED is configured to generate light having a wavelength between about 460 nm and about 470 nm.

12. A dental curing light system as recited in claim 11, further comprising a third LED configured to generate light having a wavelength between about 445 nm and about 455 nm.

13. A dental curing light system as recited in claim 10, wherein the low pass filter of the head attachment member corn comprises a dichroic coated substrate configured to reflect wavelengths greater than about 410 nm.

14. A dental curing light system, comprising:
a dental curing light device comprising:
a device body having a proximal handle portion and a distal head portion from which light is emitted during use; and
first and second LEDs disposed on or within the device body and configured for generating light, the first LED configured to generate light having a wavelength less than about 410 nm and the second LED configured to generate light having a wavelength between about 460 nm to about 470 nm,
the generated light being emitted from the distal head portion of the device body; and
a head attachment member coupleable to the distal head portion of the device body and configured so as to receive substantially all light emitted from the distal head portion of the device body,
the head attachment member comprising a low pass filter configured to filter out wavelengths greater than about 410 nm from the generated light and transmit substantially all wavelengths of light less than about 410 nm such that only wavelengths of light from the first LED are transmitted through the low pass filter and substantially no wavelengths of light from the second LED are transmitted through the low pass filter.

15. A dental curing light system as recited in claim 14, wherein the first LED is configured to generate light having a wavelength of about 405 nm.

16. A dental curing light system as recited in claim 15, further comprising a third LED configured to generate light having a wavelength between about 445 nm and about 455 nm.

17. A dental curing light system as recited in claim 14, wherein the low pass filter of the head attachment member comprises a dichroic coated substrate configured to not transmit wavelengths greater than about 410 nm.

18. A method comprising:
providing a dental curing light system as recited in claim 1;
coupling the head attachment member over the distal head portion of the device body of the dental curing light;
activating the one or more light sources of the dental curing light so as to generate light having wavelengths that are less than and greater than about 420 nm but so as to transmit only wavelengths less than about 420 nm through the low pass filter of the head attachment member;
simultaneously illuminating natural dental tissue and adjacent restorative material with light transmitted through the low pass filter of the head attachment member; and
observing the illuminated natural dental tissue and adjacent restorative material and discerning relative locations of each as a result of enhanced contrast between the natural tooth tissue and the adjacent restorative material compared to discernment between the natural tooth tissue and restorative materials that would be provided by light emitted by the one or more light sources without passing through the low pass filter.

19. A method as recited in claim 18, wherein the light sources comprise a plurality of LEDs including a first LED configured to generate light having a wavelength less than about 410 nm and a second LED configured to generate light having a wavelength between about 460 nm and about 470 nm.

20. A method as recited in claim 18, further comprising uncoupling the head attachment member from the dental curing light so that light emitted by the system includes wavelengths greater than about 420 nm and further comprising using the dental curing light to cure a camphorquinone containing photocurable dental composition.

21. A head attachment device for use with and coupleable to a dental curing light device comprising one or more light sources, comprising:

a head attachment member coupleable to a head portion of a dental curing light device and configured so as to receive substantially all light emitted from the distal head portion of the curing light device when attached thereto during use, the head attachment member comprising a low pass filter configured to filter out wavelengths of light greater than a specified wavelength and transmit substantially all wavelengths of light less than the specified wavelength, wherein the specified wavelength is about 420 nm or less such that substantially no wavelengths of light greater than the specified wavelength of about 420 nm or less are transmitted through the low pass filter and substantially all wavelengths of light less than the specified wavelength of about 420 nm or less are transmitted through the low pass filter.

22. A head attachment device as recited in claim 21, wherein the one or more light sources comprise one or more LEDs.

23. A head attachment device as recited in claim 22, wherein the one or more light sources comprise a plurality of LEDs including a first LED configured to generate light having a wavelength less than about 420 nm and a second LED configured to generate light having a wavelength greater than about 420 nm.

24. A head attachment device as recited in claim 23, wherein the first LED is configured to generate light having a wavelength of about 405 nm and the second LED is configured to generate light having a wavelength between about 460 nm and about 470 nm.

25. A head attachment device as recited in claim 24, further comprising a third LED configured to generate light having a wavelength between about 445 nm and about 455 nm.

26. A head attachment device as recited in claim 21, wherein the low pass filter of the head attachment member comprises a dichroic coated substrate configured to reflect wavelengths greater than about 420 nm.

27. A head attachment device as recited in claim 21, wherein the low pass filter is configured to filter out wavelengths greater than about 410 nm.

28. A head attachment device as recited in claim 21, wherein transmission of wavelengths that are not filtered out by the low pass filter is at least about 50%.

29. A head attachment device as recited in claim 21, wherein transmission of wavelengths that are filtered out by the low pass filter is substantially zero.

30. A head attachment device for use with and coupleable to a light device, comprising:

a head attachment member coupleable to a light device and configured so as to receive substantially all light emitted from the light device when attached thereto during use, the head attachment member comprising a low pass filter configured to filter out wavelengths of light greater than a specified wavelength and transmit substantially all wavelengths of light less than the specified wavelength, wherein the specified wavelength is about 420 nm or less such that substantially no wavelengths of light greater than the specified wavelength of about 420 nm or less are transmitted through the low pass filter and substantially all wavelengths of light less than the specified wavelength of about 420 nm or less are transmitted through the low pass filter.

* * * * *

UNITED STATES PATENT AND TRADEMARK OFFICE
CERTIFICATE OF CORRECTION

PATENT NO.        : 9,539,073 B2
APPLICATION NO.   : 14/003784
DATED             : January 10, 2017
INVENTOR(S)       : Jessop Page 1 of 1

It is certified that error appears in the above-identified patent and that said Letters Patent is hereby corrected as shown below:

In the Specification

Column 4
Line 5, change "additional the electrical" to --additional electrical--

Column 9
Line 21, insert --)-- after "Yonkers, N.Y."
Line 41, insert --.-- after "dichroic coating"

In the Claims

Column 11
Lines 57-58, change "member corn comprises" to --member comprises--

Signed and Sealed this
Twenty-fifth Day of April, 2017

Michelle K. Lee
*Director of the United States Patent and Trademark Office*